United States Patent
Hammond

(10) Patent No.: US 7,850,653 B2
(45) Date of Patent: Dec. 14, 2010

(54) ACCESS PORT INCLUDING ROTATABLE SEALS

(75) Inventor: Richard Hammond, Northford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/706,029

(22) Filed: Feb. 16, 2010

(65) Prior Publication Data
US 2010/0241081 A1  Sep. 23, 2010

Related U.S. Application Data

(60) Provisional application No. 61/162,358, filed on Mar. 23, 2009.

(51) Int. Cl.
*A61M 5/178* (2006.01)
(52) U.S. Cl. ............. 604/167.02; 604/513; 604/164.01; 604/167.01; 251/149.3
(58) Field of Classification Search .................. 604/513, 604/158, 43–44, 93.01, 164.01, 164.04–164.07, 604/164.11, 164.12, 264, 272, 167.01, 167.02, 604/167.03, 167.06, 167.04; 251/149.1, 251/149.2, 149.3
See application file for complete search history.

(56) References Cited

U.S. PATENT DOCUMENTS

| 4,000,739 | A | 1/1977 | Stevens | |
| 4,610,665 | A * | 9/1986 | Matsumoto et al. | 604/167.04 |
| 4,673,393 | A | 6/1987 | Suzuki et al. | |
| 4,798,594 | A * | 1/1989 | Hillstead | 604/167.04 |
| 5,000,745 | A | 3/1991 | Guest et al. | |
| 5,176,652 | A * | 1/1993 | Littrell | 604/167.04 |
| 5,312,363 | A | 5/1994 | Ryan et al. | |
| 5,389,081 | A * | 2/1995 | Castro | 604/167.03 |
| 5,549,565 | A * | 8/1996 | Ryan et al. | 604/167.03 |
| 6,033,426 | A | 3/2000 | Kaji | |
| 6,520,939 | B2 | 2/2003 | LaFontaine | |
| 6,551,283 | B1 | 4/2003 | Guo et al. | |
| 6,632,200 | B2 * | 10/2003 | Guo et al. | 604/247 |
| 7,081,106 | B1 * | 7/2006 | Guo et al. | 604/167.06 |
| 2003/0181858 | A1 * | 9/2003 | Lajtai et al. | 604/167.06 |
| 2004/0230161 | A1 * | 11/2004 | Zeiner | 604/167.06 |

* cited by examiner

*Primary Examiner*—Nicholas D Lucchesi
*Assistant Examiner*—Quynh-Nhu H Vu

(57) ABSTRACT

A surgical access device includes a housing; an access member extending distally from the housing and being dimensioned for positioning within tissue, and defining a longitudinal axis; and a seal assembly disposed within the housing. The seal assembly includes first and second seal components respectively having first and second seal members. Each of the first and second seal members defines a passage for passage of a surgical object in substantial sealed relation therewith. The first and second seal components are capable of relative rotation about the longitudinal axis between a first position, in which passages of the first and second seal members are in substantial alignment, and a second position where the passages of the first and second seal members are offset to inhibit the communication of fluid through the seal assembly.

9 Claims, 7 Drawing Sheets

ACCESS PORT INCLUDING ROTATABLE SEALS

CROSS REFERENCE TO RELATED APPLICATION

The present application claims the benefit of and priority to U.S. Provisional Application Ser. No. 61/162,358 filed on Mar. 23, 2009, the entire contents of which are incorporated herein by reference.

BACKGROUND

1. Technical Field

The present disclosure relates to a surgical access device that is removably insertable into a patient's tissue. More specifically, the present disclosure relates to a surgical access device including a seal assembly adapted to accommodate the insertion of surgical instrumentation and/or surgical filaments, while substantially limiting the communication of fluids therethrough.

2. Background of the Related Art

Many surgical procedures are performed through access devices, e.g., trocar and cannula assemblies. These devices incorporate narrow tubes or cannula percutaneously inserted into a patient's body, through which one or more surgical objects may be introduced to access a surgical worksite. Generally, such procedures are referred to as "endoscopic," unless the procedure is related to the examination/treatment of a joint, in which case the procedure is referred to as "arthroscopic", or to the examination/treatment of a patient's abdomen, in which case the procedure is referred to as "laparoscopic."

During these procedures, surgical filaments are often used to repair openings in skin, internal organs, blood vessels, and the like, as in the case of meniscal repair, and to join various tissues together, as in the reattachment of ligaments or tendons to bone. Additionally, a fluid, such as saline or an insufflation gas, e.g., carbon dioxide, is often introduced into the surgical worksite to increase visibility or access to tissue that is the subject of the procedure. Accordingly, the establishment and maintenance of a substantially fluid-tight seal is desirably to curtail the escape of such fluids and thereby preserve the integrity of the surgical worksite. To this end, surgical access devices generally incorporate a seal through which the surgical object and/or surgical filaments are inserted.

While many varieties of seals are known in the art, there exists a continuing need for a seal that can accommodate a variety of differently-sized surgical objects and/or surgical filaments while substantially limiting the escape of fluids.

SUMMARY

Accordingly, the present disclosure is directed to a surgical access device for use during a surgical procedure. The surgical access device includes a housing, an access member extending distally from the housing and being dimensioned for positioning within tissue, and defining a longitudinal axis; and a seal assembly disposed within the housing. The seal assembly includes first and second seal components respectively having first and second seal members. Each of the first and second seal members defines a passage for passage of a surgical object in substantial sealed relation therewith. The first and second seal components are capable of relative rotation about the longitudinal axis between a first position, in which passages of the first and second seal members are in substantial alignment, and a second position where the passages of the first and second seal members are out of alignment to inhibit the communication of fluid through the seal assembly. At least one of the first and second seal components may be at least partially receivable within the other of the first and second seal components. The seal members may be configured as multi-slit valves. The first seal component may include a first base member and a first cap extending proximally therefrom, and the second seal component may include a second base member and a second cap extending proximally therefrom. The first cap may define a transverse dimension that is smaller than a transverse dimension of the first base member, and the second cap defines a transverse dimension that is smaller than a transverse dimension of the second base member. The first base member may define an internal cavity configured and dimensioned to receive the second cap.

Detent means for releasably securing the first and second seal components in either of the first and second positions may be provided. The first seal component may include at least one detent configured and dimensioned for positioning within at least one recess on the second seal component. The seal assembly may include at least one bearing to facilitate relative rotation between the first and second seal components.

A method of performing a surgical procedure, includes the steps of:

accessing a body cavity with a surgical access device, the access device including first and second seal components respectively having first and second seal members, each of the first and second seal members defining a passage for passage of a surgical object;

positioning the first seal component and the second seal component at a first relative angular position whereby passages of the first and the second seal components are offset from each other to substantially prevent the passage of fluid;

moving, e.g., by rotating, the first seal component and the second seal component to a second relative angular position whereby passages of the first and the second seal components are in general alignment;

subsequent to the step of moving, introducing a surgical objects into the surgical worksite through the surgical access device to carry out the surgical procedure.

In another aspect of the present disclosure, a seal assembly adapted for use with a surgical access device is disclosed. The seal assembly includes first and second seal components respectively having first and second seal members. The first and second seal components are capable of relative rotation such that the seal assembly is movable from a first position, in which passages defined by the first and second seal members are in substantial alignment, to a second position, in which the passages defined by the first and second seal members are out of alignment to inhibit communication of fluid through the seal assembly.

BRIEF DESCRIPTION OF THE DRAWINGS

Various embodiments of the present disclosure are described herein below with references to the drawings, wherein.

DETAILED DESCRIPTION

Figure 1:
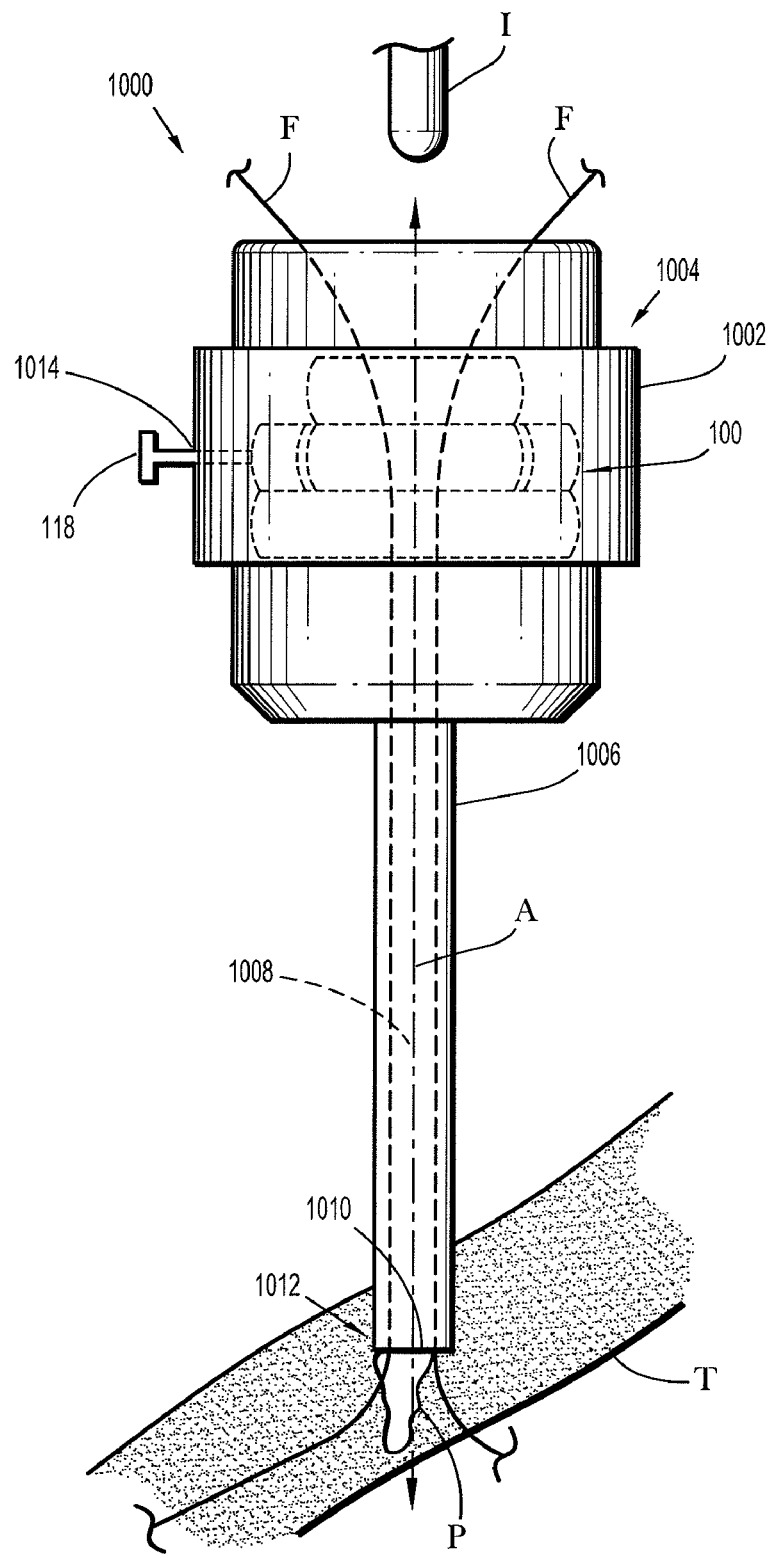
FIG. 1 is a side, schematic view of a surgical access device including one embodiment of a seal assembly that includes first and second seal components in accordance with the principles of the present disclosure.

In the drawings and in the description which follows, in which like references numerals identify similar or identical elements, the term "proximal" should be understood to refer to the end of the disclosed surgical access device, or any component thereof that is closest to a practitioner during use, while the term "distal" should be understood as referring to the end that is farthest from the practitioner during use. Additionally, the term "surgical object" should be understood to include any surgical object or instrument that may be employed during the course of surgical procedure, including but not being limited to an obturator, a surgical stapling device, or the like; the term "filament" should be understood to refer to any elongate member suitable for the intended purpose of joining tissue, including but not limited to sutures, ligatures, and surgical tape; and the term "tissue" should be understood to refer to any bodily tissue, including but not limited to skin, fascia, ligaments, tendons, muscle, and bone.

FIG. 1 illustrates a surgical access device 1000 including a housing 1002 at a proximal end 1004 thereof and an access member 1006 extending distally therefrom. The housing 1002 is configured and dimensioned to accommodate a seal assembly, one embodiment of which is shown and referred to generally by reference character 100, and may be any structure suitable for this intended purpose.

The access member 1006 is dimensioned for positioning with a percutaneous access point "P" formed in a patient's tissue "T", e.g., a patient's knee. The access member 1006 defines a passageway 1008 extending longitudinally therethrough along a longitudinal axis "A." The passageway 1008 is configured and dimensioned for the internal receipt of one or more surgical filaments "F" and/or a surgical object, or objects "I." The access member 1006 defines an opening 1010 at a distal end 1012 thereof to allow the surgical filaments "F" and the surgical object "I" to pass therethrough.

Referring now to FIGS. 2-5 as well, the seal assembly 100 will be discussed. The seal assembly 100 includes at least two seal components 102a, 102b. The seal components 102a, 102b may be formed of any suitable biocompatible and at least semi-resilient material, and may be formed through any suitable method of manufacture, including but not limited to molding, casting, and electrical discharge machining (EDM). Examples of suitable materials include, but are not limited to elastomeric materials such as natural rubber, synthetic polyisoprene, butyl rubber, halogenated butyl rubbers, polybutadiene, styrene-butadiene rubber, nitrile rubber, hydrogenated nitrile rubbers, chloroprene rubber, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermoplastic elastomers, thermoplastic vulcanizers, thermoplastic polyurethane, thermoplastic olefins, resilin, elastin, and polysulfide rubber. Forming the seal components 102a, 102b from such materials permits the seal components 102a, 102b to resiliently accommodate the insertion, manipulation, and removal of the surgical filaments "F", as well as surgical objects "I" that may vary in size.

Figure 2:
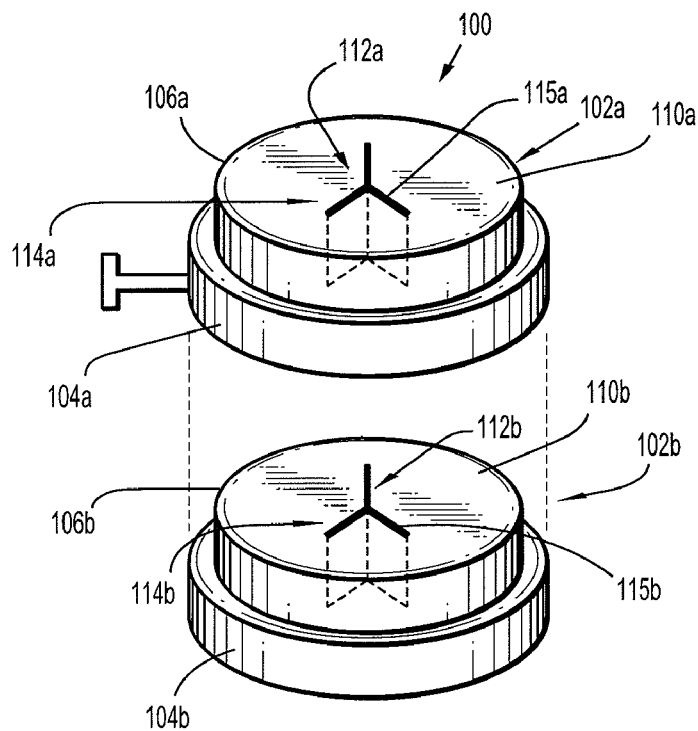
FIG. 2 is a side, perspective view of the seal assembly seen in FIG. 1 illustrating the first and second seal components separated from each other and shown in a first condition in which passages of the seal members included on the first and second seal components are in substantial alignment.
Figure 3:
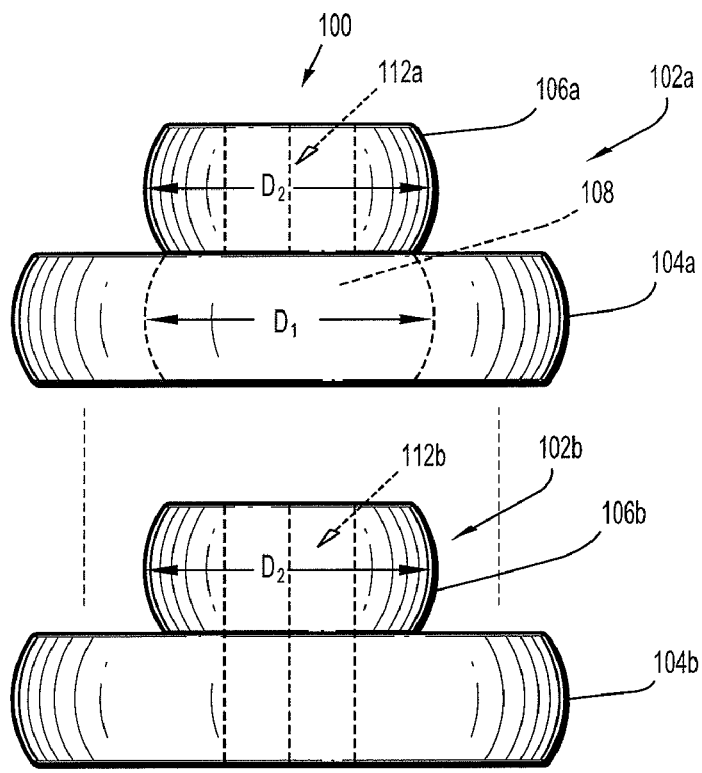
FIG. 3 is a side, schematic view of the seal assembly seen in FIG. 1 illustrating the first seal component separated from the second seal component.

The seal components 102a, 102b of the illustrated embodiments respectively include base members 104a, 104b and caps 106a, 106b. In one embodiment of the seal assembly 100, as seen in FIG. 1-3 for example, the base member 104a of the seal component 102a includes an internal cavity 108 that defines an internal transverse dimension "D1." The caps 106a, 106b extend proximally from the base members 104a, 104b, respectively, and may be either substantially solid members, as illustrated, or hollow structures that define internal spaces. The caps 106a, 106b each define an outer transverse dimension "D2" that substantially approximates the internal transverse dimension "D1" of the cavity 108 such that the seal assembly 100 can be assembled as seen in FIG. 1, i.e., such that the cap 106b of the seal component 102b is received by the internal cavity 108 defined within the base member 104a of the seal component 102a. While illustrated as substantially circular in configuration, the base members 104a, 104b and the caps 106a, 106b may exhibit any suitable geometrical configuration in alternate embodiments of the seal assembly 100.

Figure 4:
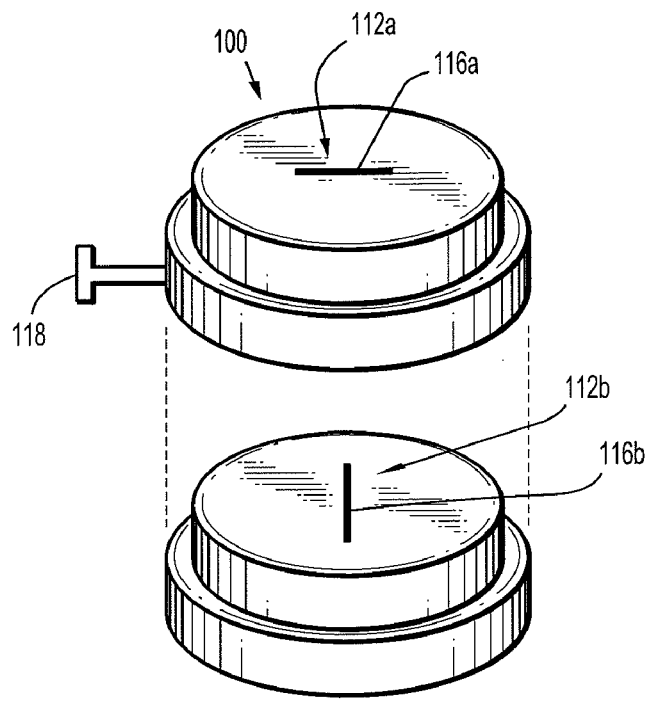
FIG. 4 is a side, perspective view of an alternate embodiment of the seal assembly seen in FIG. 1 including seal members configured as single-slit valves.

The proximal surfaces 110a, 110b of the caps 106a, 106b respectively include seal members 112a, 112b having respective passages 114a, 114b. Although depicted as multi-slit valves 115a, 115b in the embodiment of the seal assembly 100 seen in FIGS. 2 and 5, for example, the seal members 112a, 112b may include any passage suitable for the intended purpose of substantially limiting the communication of fluids, e.g., saline or insufflation gas, through the seal assembly 100, including but not limited to single slit-valves 116a, 116b, as seen in FIG. 4. The passages 114a, 114b of the seal members 112a, 112b extend through the seal components 102a, 102b (FIGS. 2-3), and are normally biased towards a closed condition, as seen in FIG. 2 for example, to provide a substantially fluid-tight seal in the absence of surgical filaments "F" and/or the surgical object "I". The seal members 112, 112b are also configured to help minimize the escape of fluid through the seal assembly 100 when the surgical filaments "F" and/or the surgical object "I" is inserted therethrough.

Figure 5:
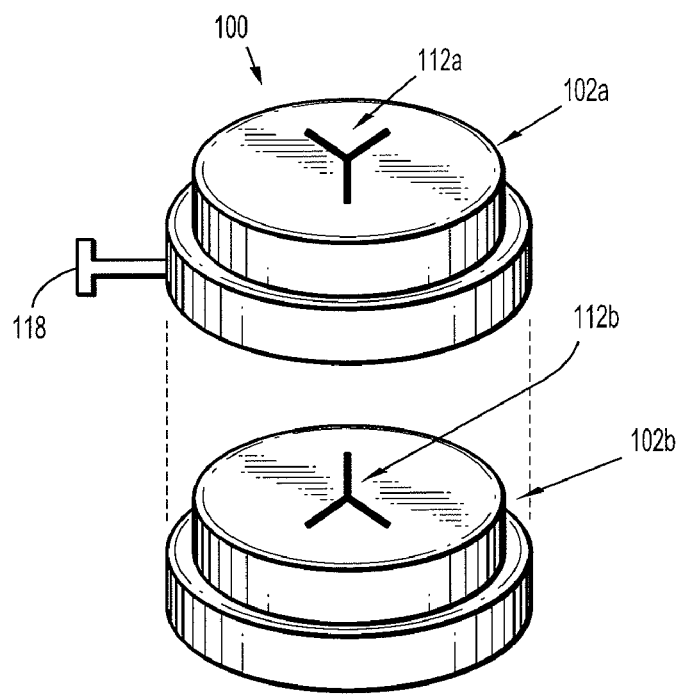
FIG. 5 is a side, perspective view of the seal assembly seen in FIGS. 1-2 illustrating the first and second seal components separated from each other and shown in a second condition in which the passages of the seal members are offset from one another.

The seal components 102a, 102b are relatively rotatable from a first position, seen in FIG. 2, in which the respective passages 114a, 114b of the seal members 112a, 112b in substantial alignment, into a second position, seen in FIG. 5, in which the respective passages 114a, 114b of the seal members 112a, 112b are offset from one another. Rotating the seal components 102a, 102b interrupts and substantially closes off the path of any fluid communicated proximally through the surgical access device 1000 (FIG. 1) to further help ensure against any substantial leakage of fluid.

Figure 6:
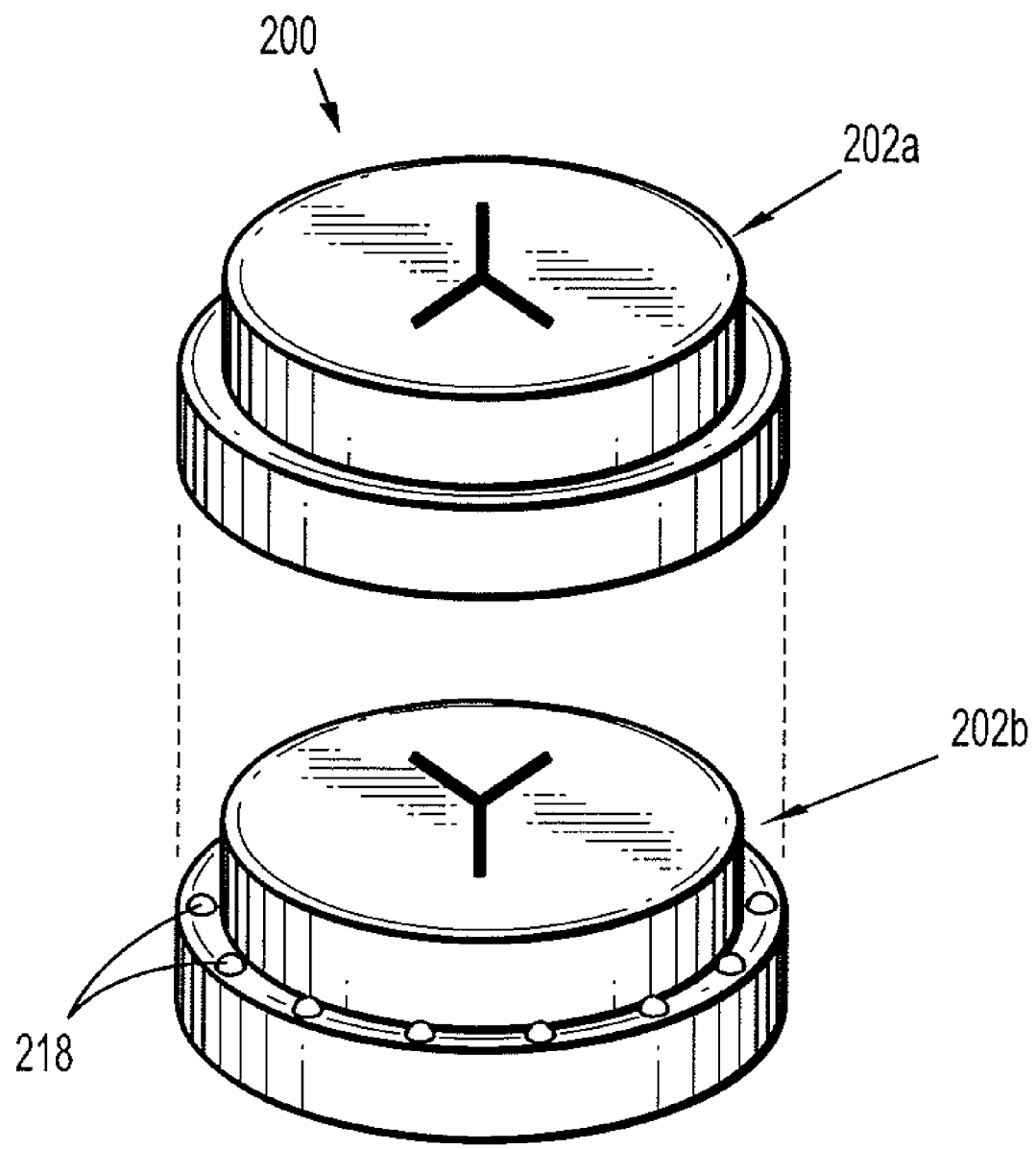
FIG. 6 is a side, perspective view of another embodiment of the seal assembly seen in FIG. 1 including a plurality of bearings to facilitate repositioning of the seal assembly between the first and second positions.
Figure 7:
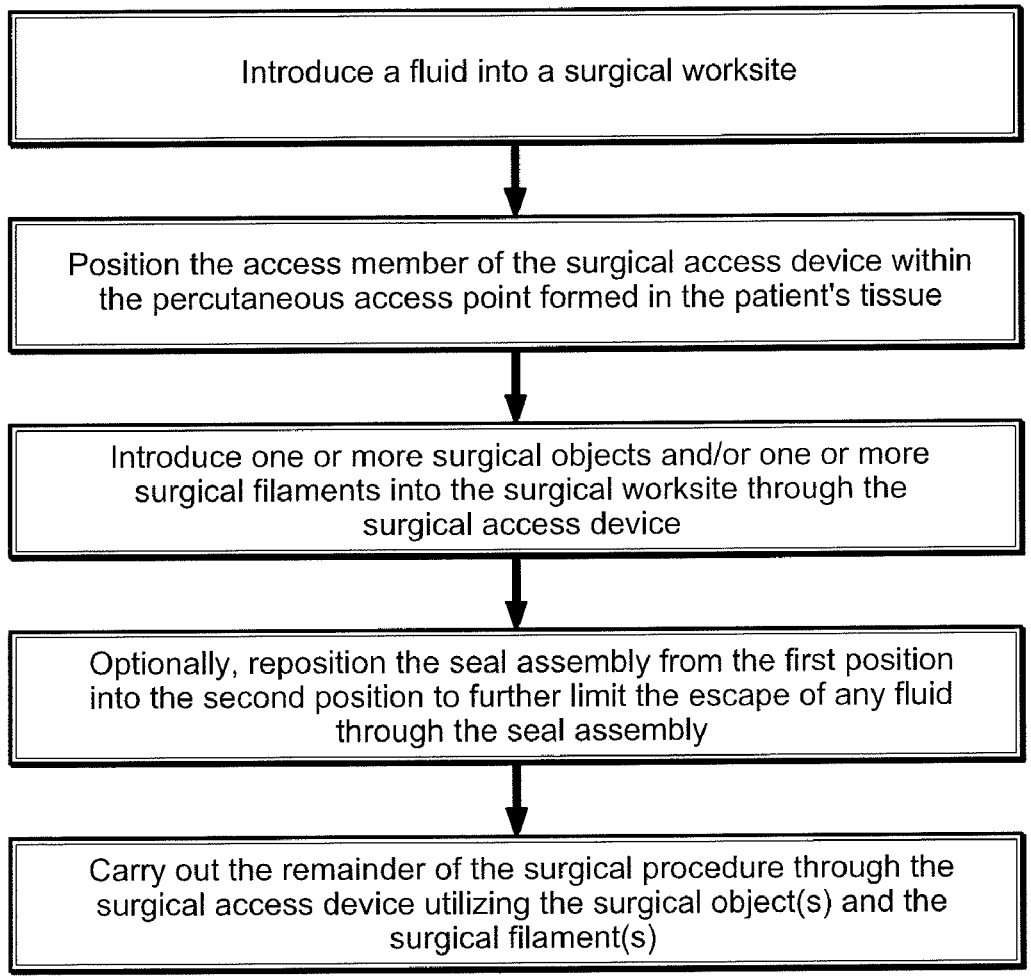
FIG. 7 is a flow chart describing a method of using the surgical access device of FIG. 1 during the course of an arthroscopic surgical procedure.

In one embodiment, as seen in FIGS. 1-5, the seal assembly 100 includes a tactile member 118 to facilitate repositioning of a portion of the seal assembly 100 between the first and second positions. The tactile member 118 can be coupled to either the seal component 102a, as seen in FIGS. 1-5, or seal component 102b, and depends outwardly therefrom through an opening 1014 (FIG. 1) in the housing 1002 of the surgical access device 1000 such that the practitioner can manually manipulate the relative position of the seal component 102a, 102b. In alternate embodiments of the seal assembly 100, relative movement between the seal component 102a, 102b may be effectuated in any suitable manner, including but not limited to the incorporation of a mechanized assembly, such as a motor and gear set. As seen in FIG. 6, in one embodiment of the seal assembly, referred to generally by reference character 200, either or both of the seal components 202a, 202b may include bearings 218, or any other suitable structure, to assist in the relative movement of the seal components 202a, 202b between the first and second positions.

With reference now to FIGS. 1-7, the use and function of the surgical access device 1000 during the course of an arthroscopic procedure will be discussed. Initially, a fluid, such as saline, is introduced into the surgical worksite. Thereafter, the access member 1006 is positioned within the percutaneous access point "P" formed in the patient's tissue "T", and the surgical object "I" and/or the surgical filament "F" are introduced into the surgical worksite by passage through the housing 1002 and the access member 1006. Either prior to the insertion of the surgical object "I" and/or the surgical filament "F" or at any other point during the course of the procedure, the practitioner may move the seal assembly 100 from the first position to the second position to regulate the leakage of any fluid. Subsequently, the practitioner can manipulate the surgical object "I" and/or the surgical filament "F" through the surgical access device 1000 to carry out the remainder of the procedure.

Figure 8:
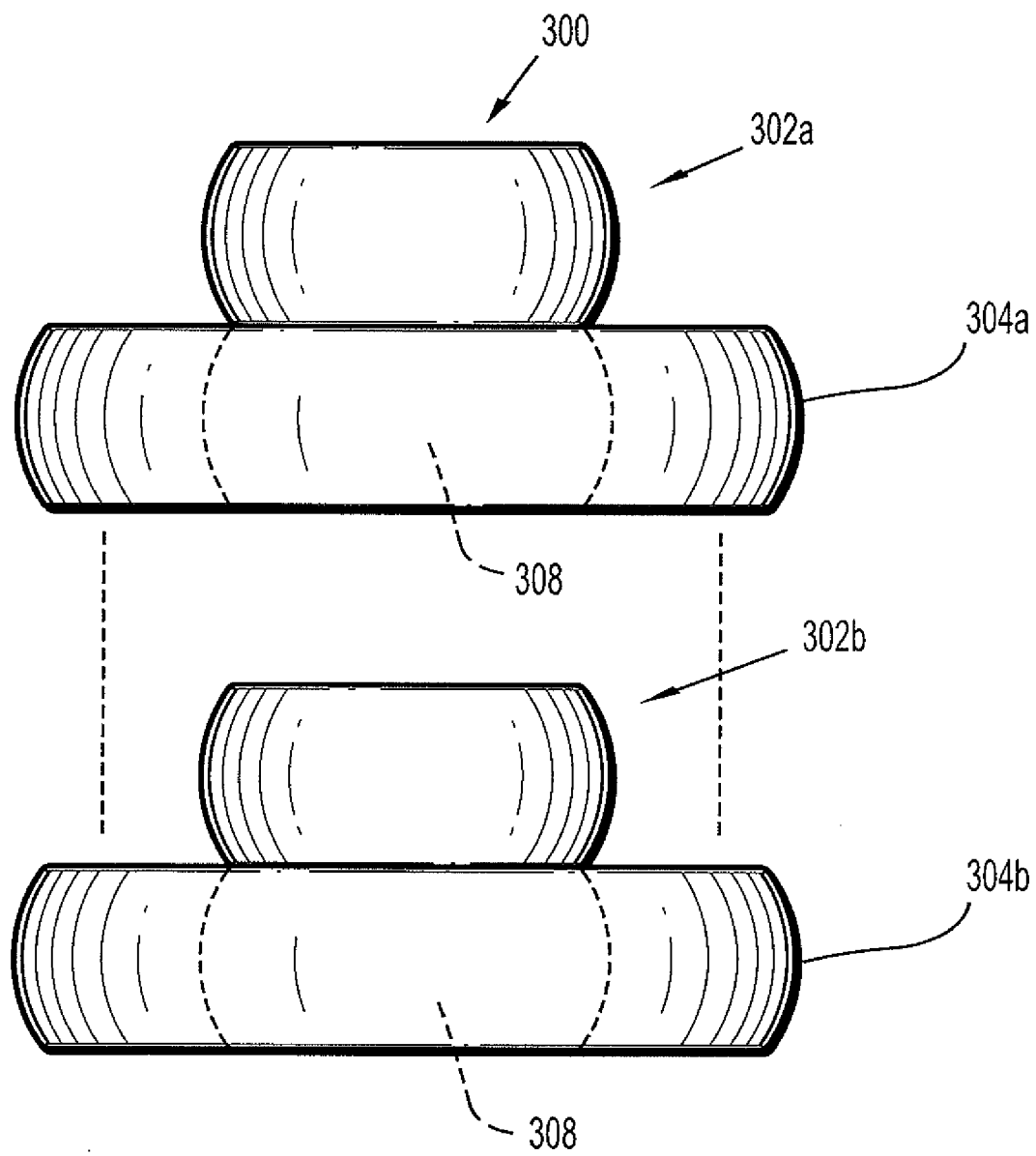
FIG. 8 is a side, schematic view of another embodiment of the seal assembly seen in FIG. 1 including first and second seal components that are substantially identical in structure shown separated from each other.
Figure 9:
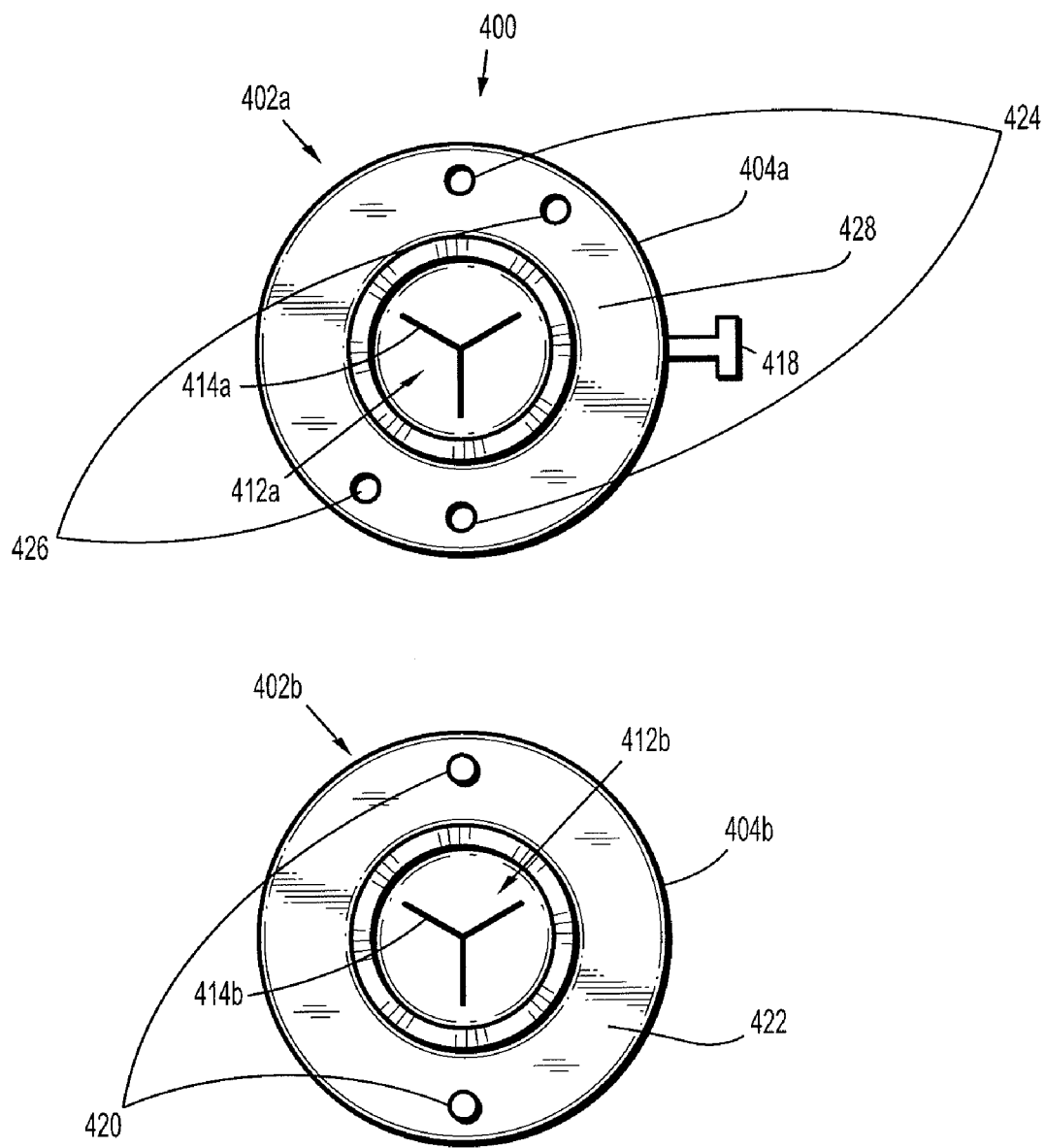
FIG. 9 illustrates another embodiment of the seal assembly seen in FIG. 1 including a first seal component with a plurality of recesses and a second seal component including a plurality of detents.

FIGS. 8-9 illustrate alternate embodiments of the seal assembly, referred to generally by reference numbers 300 and 400. The seal assembly 300 includes seal components 302a, 302b that are substantially identical in structure. Specifically, the seal components 302a, 302b include base members 304a, 304b that each defines a cavity 308. Including two seal components 302a, 302b that are substantially identical in structure allows for a substantial reduction in manufacturing costs, e.g., tooling costs, in that the total number of parts requiring fabrication is reduced by one.

The seal assembly 400 seen in FIG. 9 includes base members 404a, 404b incorporating corresponding structure that is configured to selectively maintain the first and second positions of the seal components 402a, 402b described above and respectively seen in FIGS. 2 and 5. In the embodiment of the seal assembly 400 seen in FIG. 9, the base member 404b includes a pair of detents 420 formed on a proximal surface 422 thereof that are configured and dimensioned to engage either a first pair of recess 424 or a second pair of recesses 426 formed on a distal surface 428 of the base member 404a. The detents 420 engage the first pair of recesses 424 when the seal assembly 400 is in the first position, i.e., when the respective passages 414a, 414b of the seal members 412a, 412b are in substantial alignment, and the second pair of recesses 426 when the seal assembly 400 is in the second position, i.e., when the respective passages 414a, 414b of the seal members 412a, 412b are offset from each other. The detents 422 and the respective first and second pairs of recesses 424, 426 are configured and dimensioned such that the first and second positions are maintained until a predetermined force has been applied to seal assembly 400, e.g., through use of the tactile member 418.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure. For example, although each embodiment of the seal assembly is illustrated as including two seal components, embodiments including three or more seal components arranged in accordance with the manner described above are also within the scope of the present disclosure. Additionally, persons skilled in the art will appreciate that the features illustrated or described in connection with one embodiment may be combined with those of another, and that such modifications and variations are also intended to be included within the scope of the present disclosure.

What is claimed is:

1. A surgical access device for use during a surgical procedure, which comprises:
   a housing;
   an access member extending distally from the housing and being dimensioned for positioning within tissue, the housing and the access member defining a longitudinal axis; and
   a seal assembly disposed within the housing, the seal assembly including first and second seal components respectively having first and second seal members, each of the first and second seal members defining a passage for passage of a surgical object in substantial sealed relation therewith, the first and second seal components being capable of relative rotation within the housing and about the longitudinal axis between a first position, in which passages of the first and second seal members are in substantial alignment, and a second position where the passages of the first and second seal members are out of alignment to inhibit the communication of fluid through the seal assembly.

2. The surgical access device of claim 1, wherein at least one of the first and second seal components is at least partially receivable within the other of the first and second seal components.

3. The surgical access device of claim 1, wherein the seal members are configured as multi-slit valves.

4. The surgical access device of claim 1, wherein the first seal component includes a first base member and a first cap extending proximally therefrom, and the second seal component includes a second base member and a second cap extending proximally therefrom.

5. The surgical access device of claim 4, wherein the first cap defines a transverse dimension that is smaller than a transverse dimension of the first base member, and the second cap defines a transverse dimension that is smaller than a transverse dimension of the second base member.

6. The surgical access device of claim 5, wherein the first base member defines an internal cavity configured and dimensioned to receive the second cap.

7. The surgical access device of claim 1, including detent means for releasably securing the first and second seal components in either of the first and second positions.

8. The surgical access device of claim 7, wherein the first seal component includes at least one detent configured and dimensioned for positioning within at least one recess on the second seal component.

9. The surgical access device of claim 1, wherein the seal assembly includes at least one bearing to facilitate relative rotation between the first and second seal components.

* * * * *